(12) United States Patent
Lavi

(10) Patent No.: US 7,927,563 B1
(45) Date of Patent: Apr. 19, 2011

(54) KIT FOR SEPARATION OF BIOLOGICAL FLUIDS

(75) Inventor: Gilad Lavi, Rishon Lezion (IL)

(73) Assignee: Cytomedix, Inc., Rockville, MD (US)

( * ) Notice: Subject to any disclaimer, the term of this patent is extended or adjusted under 35 U.S.C. 154(b) by 0 days.

(21) Appl. No.: 12/900,127

(22) Filed: Oct. 7, 2010

Related U.S. Application Data

(60) Provisional application No. 61/272,609, filed on Oct. 13, 2009.

(51) Int. Cl.
*B01L 3/00* (2006.01)
*B01L 3/14* (2006.01)
*G01N 1/18* (2006.01)
*B01D 21/26* (2006.01)
*C02F 1/38* (2006.01)

(52) U.S. Cl. ........ 422/548; 422/430; 422/547; 422/549; 436/177; 210/787

(58) Field of Classification Search .................. None
See application file for complete search history.

(56) References Cited

U.S. PATENT DOCUMENTS

| | | |
|---|---|---|
| 3,596,652 A | 8/1971 | Winkelman |
| 3,931,010 A | 1/1976 | Ayres et al. |
| 3,937,211 A | 2/1976 | Merten |
| 4,361,155 A | 11/1982 | Anastasio |
| 4,464,254 A | 8/1984 | Dojki et al. |
| 4,660,569 A | 4/1987 | Etherington |
| 4,936,315 A | 6/1990 | Lineback |
| 4,957,637 A | 9/1990 | Cornell |
| 4,961,432 A | 10/1990 | Guirguis |
| 5,032,117 A | 7/1991 | Motta |
| 5,273,542 A | 12/1993 | Blake, III |
| 5,374,250 A | 12/1994 | Dixon |
| 5,569,193 A | 10/1996 | Hofstetter et al. |
| 5,577,513 A | 11/1996 | Van Vlasselaer |
| 5,592,948 A | 1/1997 | Gatten |
| 5,779,668 A * | 7/1998 | Grabenkort .................. 604/89 |
| 5,873,841 A | 2/1999 | Brannon |
| 6,123,687 A | 9/2000 | Simonyi et al. |
| 6,364,869 B1 | 4/2002 | Bonaldo |
| 6,410,334 B1 | 6/2002 | Schmolz |
| 7,179,391 B2 * | 2/2007 | Leach et al. ................ 210/782 |
| 7,195,606 B2 | 3/2007 | Ballin |
| 2003/0205538 A1 | 11/2003 | Dorian et al. |
| 2004/0167004 A1 | 8/2004 | Jorgensen et al. |
| 2005/0101920 A1 | 5/2005 | Keane et al. |
| 2005/0123895 A1 | 6/2005 | Freund |

(Continued)

FOREIGN PATENT DOCUMENTS

CN 200973714 11/2007

(Continued)

*Primary Examiner* — Jill Warden
*Assistant Examiner* — Charles Hammond
(74) *Attorney, Agent, or Firm* — Stephen A. Bent; Foley & Lardner LLP

(57) ABSTRACT

For containing a biological fluid and draining a constituent of the biological fluid, a kit includes a barrel, a piston assembly, a removable element, which is configured to move the piston assembly, a drainage element, which interacts with the piston assembly, and an interacting element, which interacts with the piston assembly. The kit allows for fluid separation without risk of contamination from the biological fluid itself or contamination of the biological fluid itself. Further, the kit offers the advantage of involving no needles or other sharp elements.

10 Claims, 13 Drawing Sheets

U.S. PATENT DOCUMENTS

| | | |
|---|---|---|
| 2005/0261620 A1 | 11/2005 | Ballin |
| 2006/0100590 A1 | 5/2006 | Thorne et al. |
| 2006/0175242 A1 | 8/2006 | Dorian et al. |
| 2006/0243676 A1 | 11/2006 | Swift et al. |
| 2006/0273050 A1 | 12/2006 | Higgins et al. |
| 2007/0075016 A1 | 4/2007 | Leach |
| 2008/0082055 A1 | 4/2008 | Lloyd et al. |
| 2008/0166421 A1 | 7/2008 | Buhr et al. |
| 2009/0221075 A1 | 9/2009 | Dorian et al. |

FOREIGN PATENT DOCUMENTS

| | | |
|---|---|---|
| DE | 3025800 A1 | 2/1982 |
| DE | 44 45 030 A1 | 6/1996 |
| EP | 2 077 115 A1 | 7/2009 |
| JP | 2002-204906 | 7/2002 |
| JP | 2008-104789 | 5/2008 |
| JP | 2008-232876 | 10/2008 |
| KR | 2003-0064491 | 8/2003 |
| WO | WO 94/00169 | 1/1994 |
| WO | WO 96/05770 | 2/1996 |
| WO | WO 02/067778 A2 | 9/2002 |
| WO | WO 2004/009207 A1 | 1/2004 |
| WO | WO 2005/055814 A2 | 6/2005 |
| WO | WO 2005/065752 A1 | 7/2005 |
| WO | WO 2005/087292 A1 | 9/2005 |
| WO | WO 2006/007711 A1 | 1/2006 |
| WO | WO 2006/030749 A1 | 3/2006 |
| WO | WO 2007/000986 A1 | 1/2007 |
| WO | WO 2008/050688 A1 | 5/2008 |

* cited by examiner

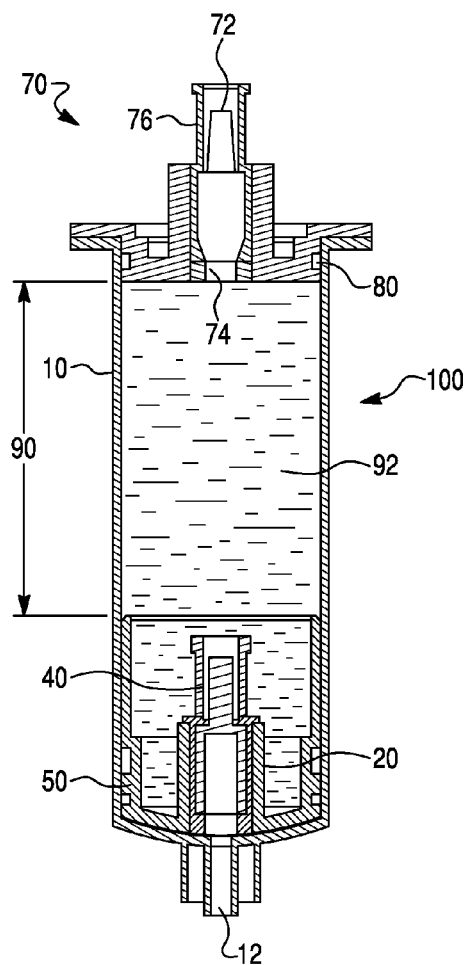
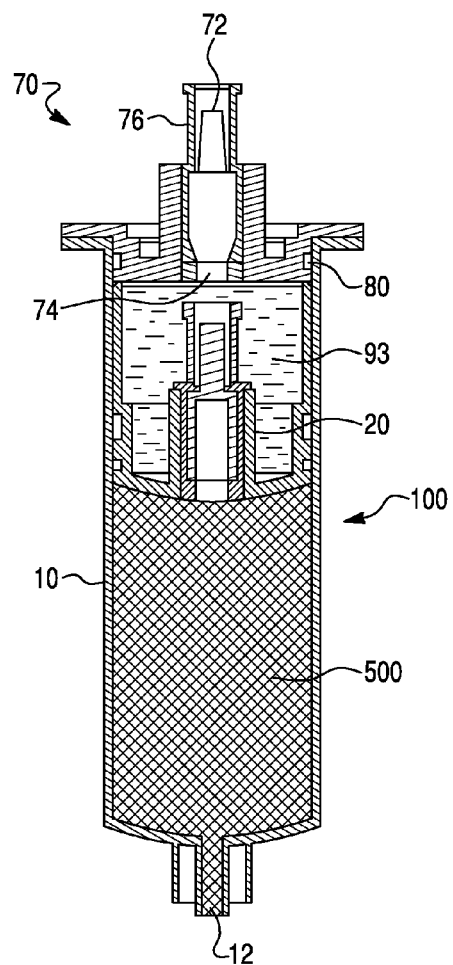

Fig. 8A
Fig. 8B
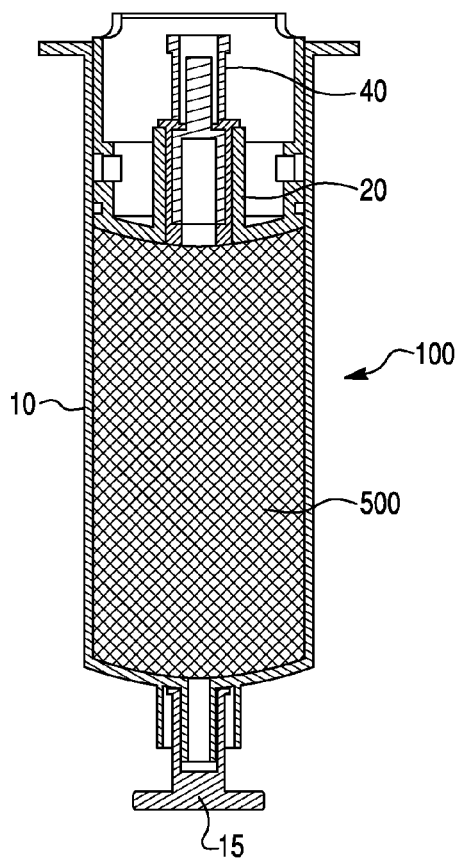
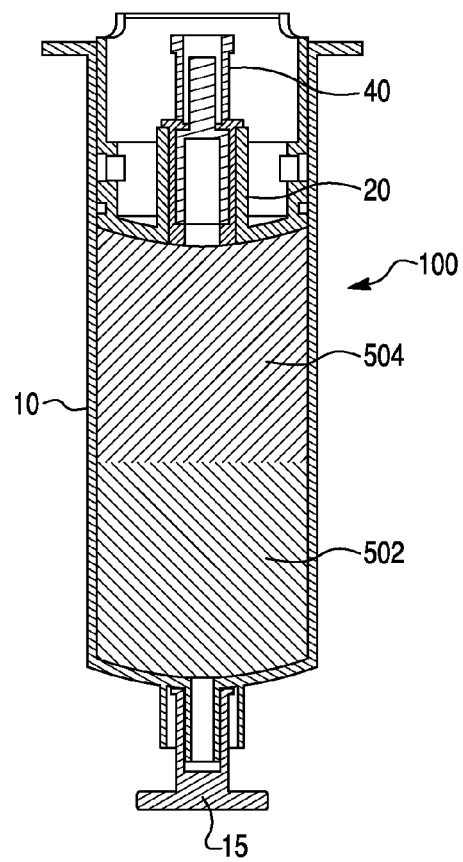

KIT FOR SEPARATION OF BIOLOGICAL FLUIDS

CROSS-REFERENCE TO RELATED PATENT APPLICATIONS

This application claims priority from U.S. Provisional Application No. 61/272,609, filed Oct. 13, 2009, which is incorporated herein by reference in its entirety.

BACKGROUND OF THE INVENTION

The present invention relates generally to a kit for containing biological fluid and draining a constituent of the biological fluid.

Conventional kits, such as those described in EP 2077115 and U.S. Pat. No. 6,123,687, have been used to house biological fluids, drain a constituent of the biological fluid, and/or separate the biological fluid into constituents. Conventional kits present disadvantages associated with the use sharp elements, such as needles, or with enabling fluid separation at a substantial risk of contamination, either of the kit from the biological fluid or of the biological fluid itself.

SUMMARY OF THE INVENTION

In view of these disadvantages and other drawbacks to the conventional technology, the present invention provides a kit for containing biological fluid and draining a constituent of the biological fluid. The kit comprises a barrel, a piston assembly, a removable element, a drainage element, and an interacting element and a sealing element. The barrel includes a first static opening for receiving the biological fluid. The piston assembly is disposed within the barrel and comprises a shut-off valve. The shut-off valve is configured to form a second movable opening for receiving or draining the constituent when the shut-off valve is engaged to be open. The removable element is configured to aspirate the biological fluid through the first static opening and is configured to move the piston assembly, without engaging the shut-off valve, so that the first static opening receives the biological fluid. The drainage element is configured to engage the shut-off valve, such that the shut-off valve opens and the second movable opening receives the constituent. The interacting element is configured to engage the shut-off valve, such that the shut-off valve opens and the second moveable opening receives a substance. At least a portion of the interacting element is positioned in the barrel. The sealing element is configured to seal the first static opening when the shut-off valve opens. The interacting element comprises a rod and an adapter element. A portion of the adapter element is positioned in the rod, that is configured to transport the substance.

It is to be understood that both the foregoing general description and the following detailed description are exemplary and explanatory only, and are not restrictive.

BRIEF DESCRIPTION OF THE DRAWINGS

These and other features, aspects, and advantages of the present embodiments will become apparent from the following description and the accompanying exemplary embodiments shown in the drawings, which are synopsized below.

FIG. 6A is a cross-sectional view of the component of the kit of FIG. 1C before aspiration of the biological fluid and showing the distance the piston assembly moves in the barrel and the predetermined volume in the barrel.

FIG. 6B is a cross-sectional view of the component of the kit of FIG. 1C after aspiration of the biological fluid.

FIG. 8A is a cross section of the component of the kit of FIG. 1A before the biological fluid is separated into constituents.

FIG. 8B is a cross section of the component of the kit of FIG. 1A after the biological fluid is separated into constituents.

DETAILED DESCRIPTION

Figure 1A:
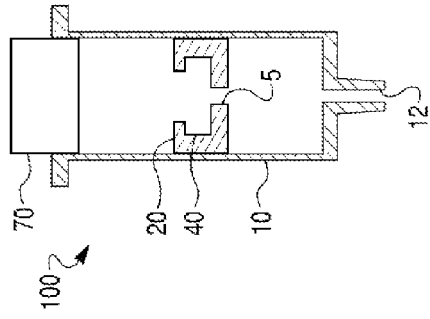
FIG. 1A is a schematic illustration of a component of a kit, showing a barrel and a piston assembly, for containing a biological fluid and draining a constituent of the biological fluid.
Figure 1B:
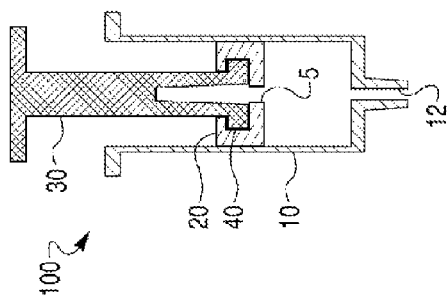
FIG. 1B is a schematic illustration of a component of the kit of FIG. 1A, including a first removable element.
Figure 1C:
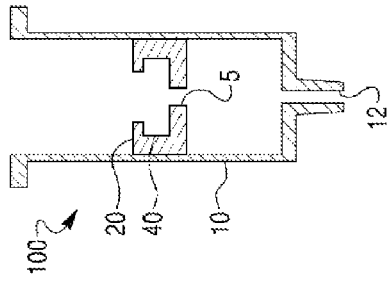
FIG. 1C is a schematic illustration of a component of the kit of FIG. 1A, including a second removable element.
Figure 1D:
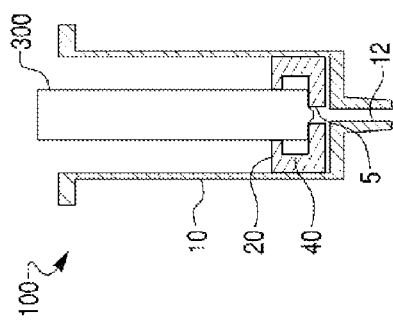
FIG. 1D is a schematic illustration of a component of the kit of FIG. 1A, including a drainage element.
Figure 1E:
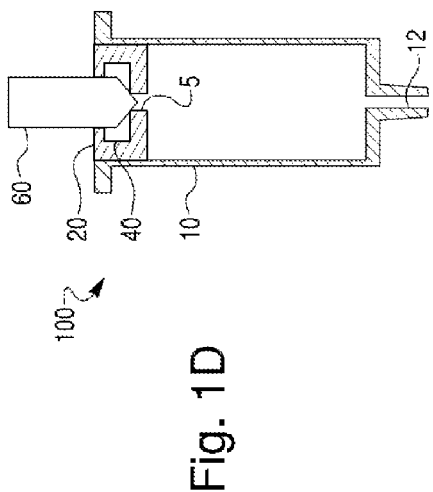
FIG. 1E is a schematic illustration of a component of the kit of FIG. 1A, including an interacting element.

For containing a biological fluid and draining a constituent of the biological fluid, a kit is provided (components of the kit shown in FIGS. 1A-1E) that includes a barrel 10, a piston assembly 20, a removable element 30, 70, which is configured to move the piston assembly 20, a drainage element 60, which interacts with the piston assembly 20, and an interacting element 300, which interacts with the piston assembly 20. For the purposes of this application, components of the kit will collectively be referred to as reference numeral 100.

The biological fluid passes through a first opening 12 or distal port 12 when the first opening 12 is connected to the biological fluid and when the piston assembly 20 moves to aspirate the biological fluid. The biological fluid, such as blood, is contained in the barrel 10, which has the first opening 12. The first opening 12 may be a first static opening 12 for receiving the biological fluid. The piston assembly 20 includes a shut-off valve 40, disposed within the barrel 10, that is configured to form a moveable second opening 5, through which the same or a different biological fluid can pass when the shut-off valve 40 is open, which happens when the shut-off valve 40 is engaged by the drainage element 60. Conversely, the shut-off valve 40 is closed when it is not so engaged. More specifically, the shut-off valve 40 is engaged when the drainage element 60 engages the shut-off valve 40. The shut-off valve 40 is not engaged by the removable element 30, 70.

Alternately, the kit 100 may include the interacting element 300, which serves initially as a conduit for a substance, such as an anti-coagulant, that becomes mixed with the biological fluid when introduced into the barrel 10. The interacting element 300 engages the shut-off valve 40 to open the shut-off valve 40. When the interacting element 300 engages the shut-off valve 40, the first opening 12 is sealed. Sealing may be provided by a one way valve 350, applied to the first opening 12, that only allows fluid to enter the barrel 10 via the first opening 12 or by a plug (not shown) that plugs the first opening 12.

Kit 100 thus allows for fluid separation without risk of contamination from the biological fluid itself or contamination of the biological fluid itself. Further, the kit 100 offers the advantage of involving no needles or other sharp elements. For the purposes of the application, the distal end/direction refers to the end/direction farther away from the operator of the kit 100 and the proximal end/direction refers to the end/direction closest to the operator of the kit 100. Additionally, for the purposes of the application, the biological fluid may be any suitable fluid. Preferably the biological fluid is platelet-rich plasma.

Figure 2A:
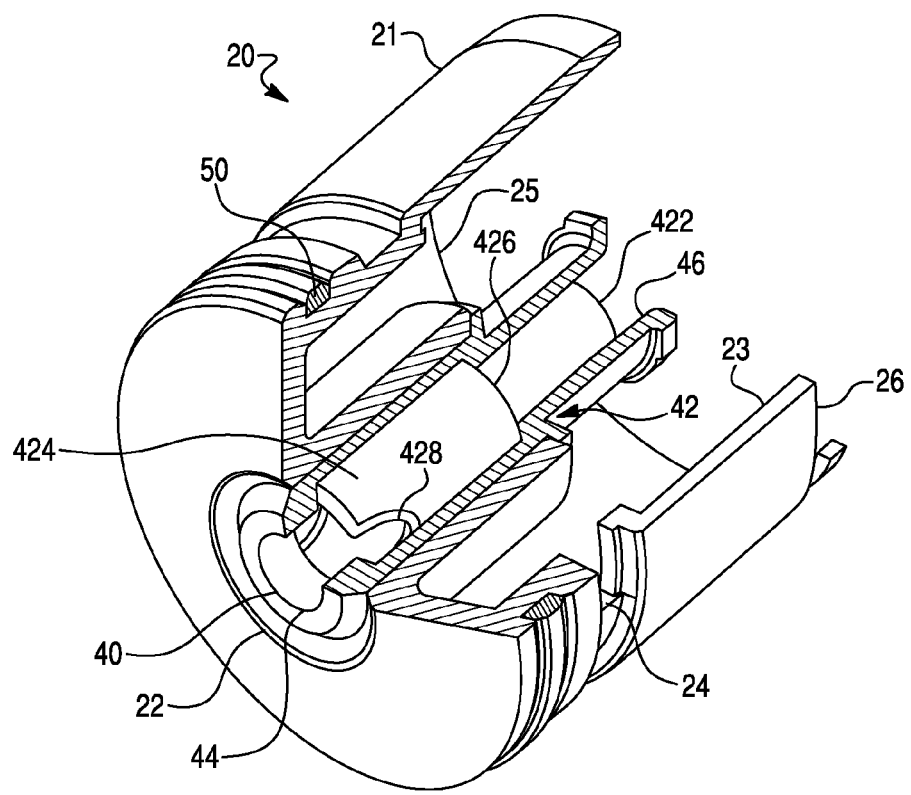
FIG. 2A is side, partial cross section, perspective view of the piston assembly of FIGS. 1A-1E.
Figure 2B:
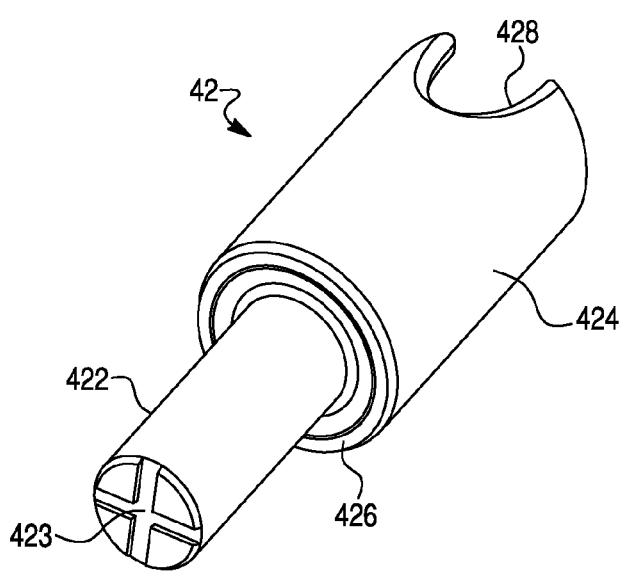
FIG. 2B is a side, elevated view of the active element of FIG. 2A.

Referring to FIGS. 2A-2B, the piston assembly 20 includes a piston housing 21 and a housing bore 23. The piston housing 21 is the outermost side boundary of the piston assembly 20, which contains a shut-off valve 40, and the housing bore 23 is the innermost side boundary of the piston assembly 20, which contains a shut-off valve 40.

The piston assembly 20 includes a seal 50 and a shut-off valve 40 or valve assembly 40. The seal 50 may be any suitable seal, for example an O-ring seal 50. The shut-off valve 40 is housed in a housing 44, where the housing 44 is positioned within a valve cavity of the piston assembly 20 by any suitable mechanism. For example, the valve housing 44 may be glued to the cavity 22.

The shut-off valve 40 may include an active element 42 or a flexible element 42 that is configured to open the shut-off valve 40. The active element 42 may be positioned with the valve housing 44. The active element 42 may include a luer connector 46, a triggering neck 422, a collar 424, and a sealing lip 426. The luer connector 46 is configured to engage an external element (e.g., a drainage element or an interacting element) in order that the active element 42 is able to open the shut-off valve 40. The sealing lip 426 connects the triggering neck 422 to the collar 424. The collapsible collar 424 may be a tubular element that behaves similar to a spring. The collar 424 may provide pressure over the sealing lip 426 to keep the shut-off valve 40 closed. When the luer connector 46 is engaged by the drainage element 60 or the interacting element 300, the triggering neck 422 is pushed toward the collar 424. The collar 424 stops providing pressure to the sealing lip 426 and the shut-off valve 40 opens. In contrast, when the luer connector 46 is not engaged by the drainage element 60 or the interacting element 300, the triggering neck 422 is not pushed toward the collar 424 and the collar 424 provides pressure over the sealing lip 426, thereby keeping the shut-off valve 40 closed. The active element 42 also may include triggering neck slits 423 and a flow path detent 428. The triggering neck slits 423 prevent any potential sealing of the drainage element or the interacting element if the drainage element or the interacting element interacts with the active element 42. The flow path dent 428 ensures a proper fluid path to the first static opening 12 when the triggering neck 422 is pushed toward the collar 424. The flow path dent 428 ensures the proper fluid path by preventing the collar 424 from sealing a surrounding cavity of the active element 42 when the collar 424 is collapsing. The active element 42 may be made of any suitable material, e.g., a medical grade rubber.

The piston assembly 20 may additionally include snapping traps 24, a rod release recess 26, and an axial stop 25. The snapping traps 24 may house engaging elements of an external element (e.g., the removable element 30), where the engaging elements snap into the snapping traps 24. When the engaging elements snap into the snapping traps 24, the snapping traps 24 help maintain the connection of the removable element 30 to the piston assembly 20. The rod release recess 26 helps an operator of the kit 100 find the location where the operator should press to release the engaging elements, which snap into the snapping traps 24, from the snapping traps 24. The rod release recess 26 is only accessible to the operator of the kit 100 when the biological fluid has completely aspirated into the barrel 10. The rod release recess 26 also guides the insertion of the removable element 30 in the barrel 10 to ensure that the engaging elements snap into the snapping traps 24. Additionally, the rod release recess 26 provides a large enough surface for an operator's finger, as opposed to merely the tip of the operator's finger, to exert pressure on the removable element 30 so as to release the engaging elements from the snapping traps 24. The axial stop 25 interacts with the removable element 30 by positioning the removable element 30 with respect to the piston assembly 20.

Figure 3A:
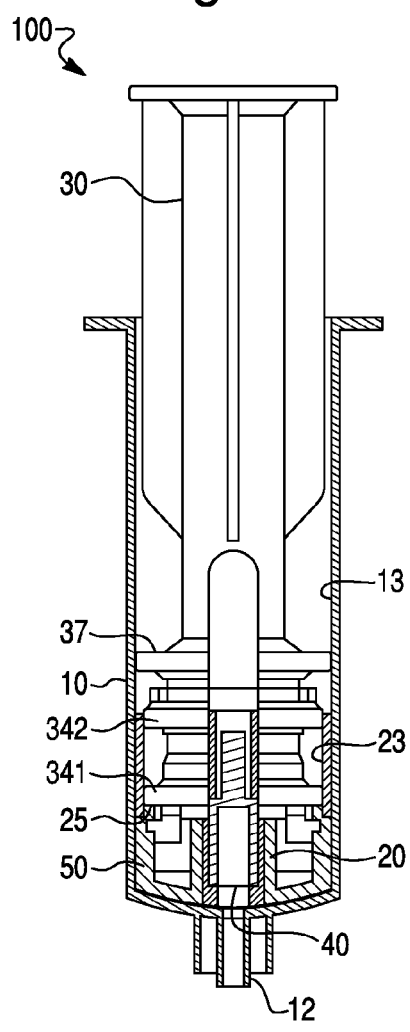
FIG. 3A is a cross-sectional view of the component of the kit of FIG. 1B before aspiration of the biological fluid.

The removable element 30, 70 is configured to aspirate biological fluid through the first static opening 12. Additionally, the removable element 30, 70 is configured to move the piston assembly 20, without engaging the shut-off valve 40, so that the first static opening 12 receives the biological fluid. FIGS. 3A-4 show one example of a removable element 30. FIGS. 5-7B show a second example of a removable element 70.

Referring to FIGS. 3A-4, a removable element 30 is shown that includes a shaft 39, snapping elements 32, and annular elements 341, 342, 37. The removable element 30 may be any suitable element capable of being removed from the barrel 10. For example, the removable element 30 may be a rod 30. At least a portion of the removable element 30 (e.g. an accessible element 37 or elongating ribs 391) is able to fit within the barrel 10.

The shaft 39 of the removable element 30 may include elongating ribs 391. The elongating ribs 391 may stabilize the removable element 30 when a portion of the removable element 30 is within the barrel 10. The shaft 39 may include one or more elongating ribs 391. For example, as shown in FIG. 4, the shaft 39 may include four elongating ribs 391.

The snapping elements 32 are coupled to the shaft 39 and are configured to engage the piston assembly 20 because the snapping elements 32 are flexible. A flexibility notch 38, of the removable element 30, enables the snapping elements 32 to be flexible. The flexibility notch 38 enables the snapping elements 32 to be flexible because two arms 401, 402 are configured to deflect and break off from an axial cross section of the shaft 39. The arms are relatively stiff when an axial force is applied to the arms 401, 402 but are relatively flexible when a radial force is applied to the arms 401, 402. The arms 401, 402 carry the annular elements 341, 342, 37. When the snapping elements 32 engage the piston assembly 20, the snapping elements 32 fit within the snapping traps 24 of the piston assembly 20.

The annular elements 341, 342, 37 help stabilize the removable element 30 within the piston assembly 20. The stabilizing element 341 or distal stabilizing rib 341 is coupled to the shaft 30 and is adjacent to the snapping elements 32. The stabilizing element 341 is configured to restrict radial movement of the shaft when the snapping elements 32 engage the piston assembly 20. For example, when the snapping elements 32 engage the piston assembly 20, the stabilizing elements 341 interact with the axial stop 25 of the piston assembly 20. The axial stop 25 axially positions the stabilizing elements 341. The stabilizing element 341 may also provide radial support for the removable element 30 when at least a portion of the removable element 30 is within the piston assembly 20. When the stabilizing element 341 provides the radial support, stabilizing element 341 and proximal stabilizing rib 342 may be centered by the bore 23 of the piston assembly 20.

The release knob 37 or accessible element 37 provides radial stabilization of the removable element 30 when at least a portion of the removable element 30 is within the piston assembly 20 located within the barrel 10 (see FIG. 3A) and is configured to disengage the snapping elements 32 from the piston assembly 20. The release knob 37 can only disengage the snapping elements 32 when the barrel 10 contains a sufficient amount of the biological fluid 500. The release knob 37 functions as a pressing knob that manually releases the snapping elements 32 from the piston assembly 20 when a suitable radial pressure is exerted on the release knob 37. A suitable pressure, however, can only be exerted on the release knob 37 when a sufficient amount of biological fluid 500 has entered the barrel 10 through the first static opening 12. Generally, a sufficient amount of biological fluid 500 has entered the barrel 10 when the removable element 30 is fully extracted from the barrel 10. As shown, for example in FIG. 3A, a suitable pressure cannot be exerted on the release knob 37 because a portion of the removable element 30 is within the barrel 10. However, as shown for example in FIG. 3B, a suitable pressure can be exerted on the release knob 37 because the removable element 30 is fully extracted from the barrel 10. The release knob 37 also allows internal sliding of the removable element 30 within a bore 13 of the barrel 10.

The removable element 30 may also include a finger flange 36 or flange 36 (FIG. 4). The finger flange 36 allows a user to grip the removable element 30. The flange 36 is similar to a conventional flange of a rod of a syringe.

Figure 3B:
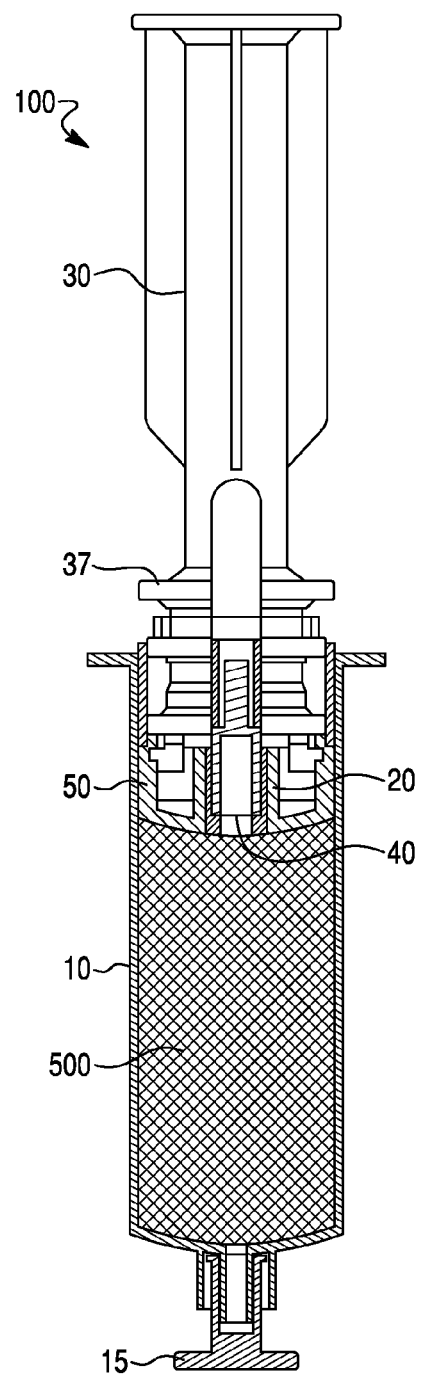
FIG. 3B is a cross-sectional view of the component of the kit of FIG. 1B after aspiration of the biological fluid and after a plug has been inserted into a first opening.
Figure 4:
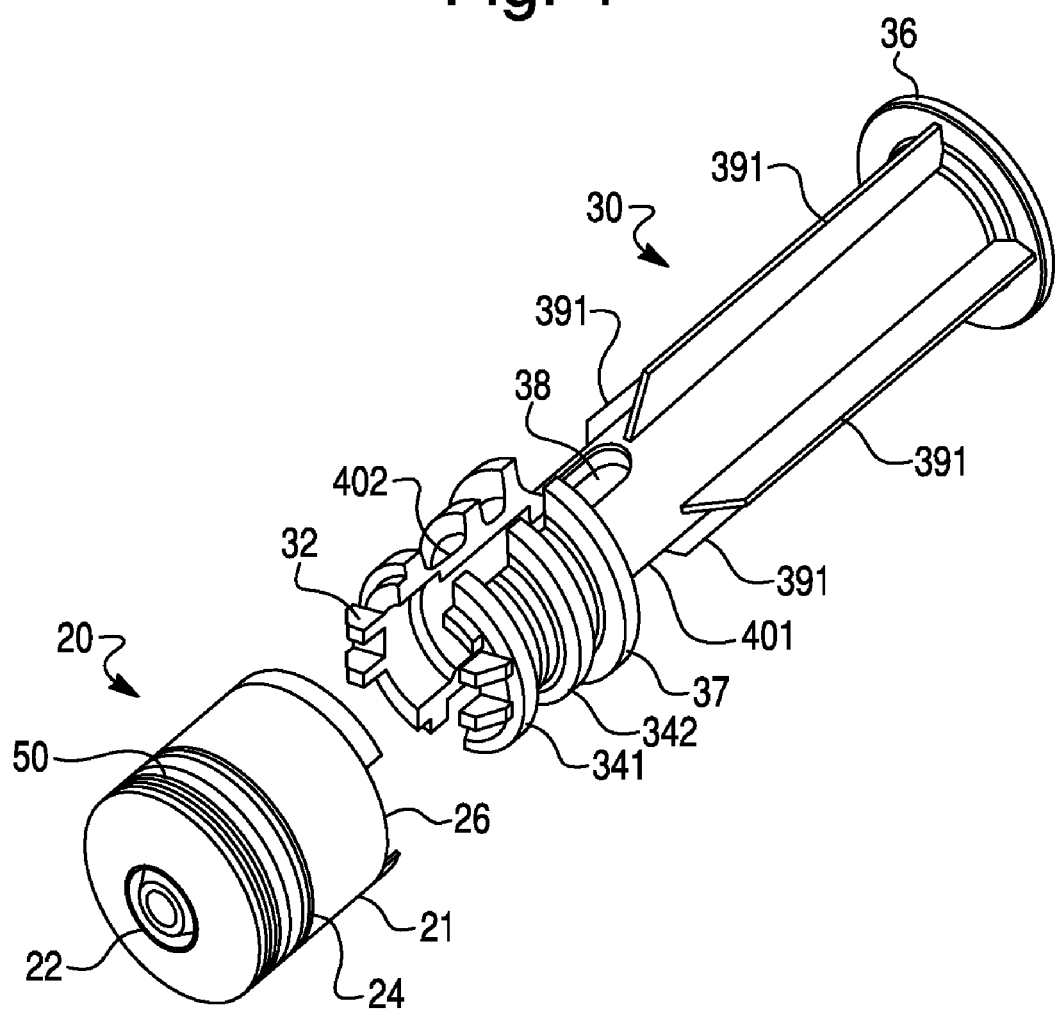
FIG. 4 is a side, partially exploded perspective view of the piston assembly and the removable element of FIG. 1B.
Figure 5:
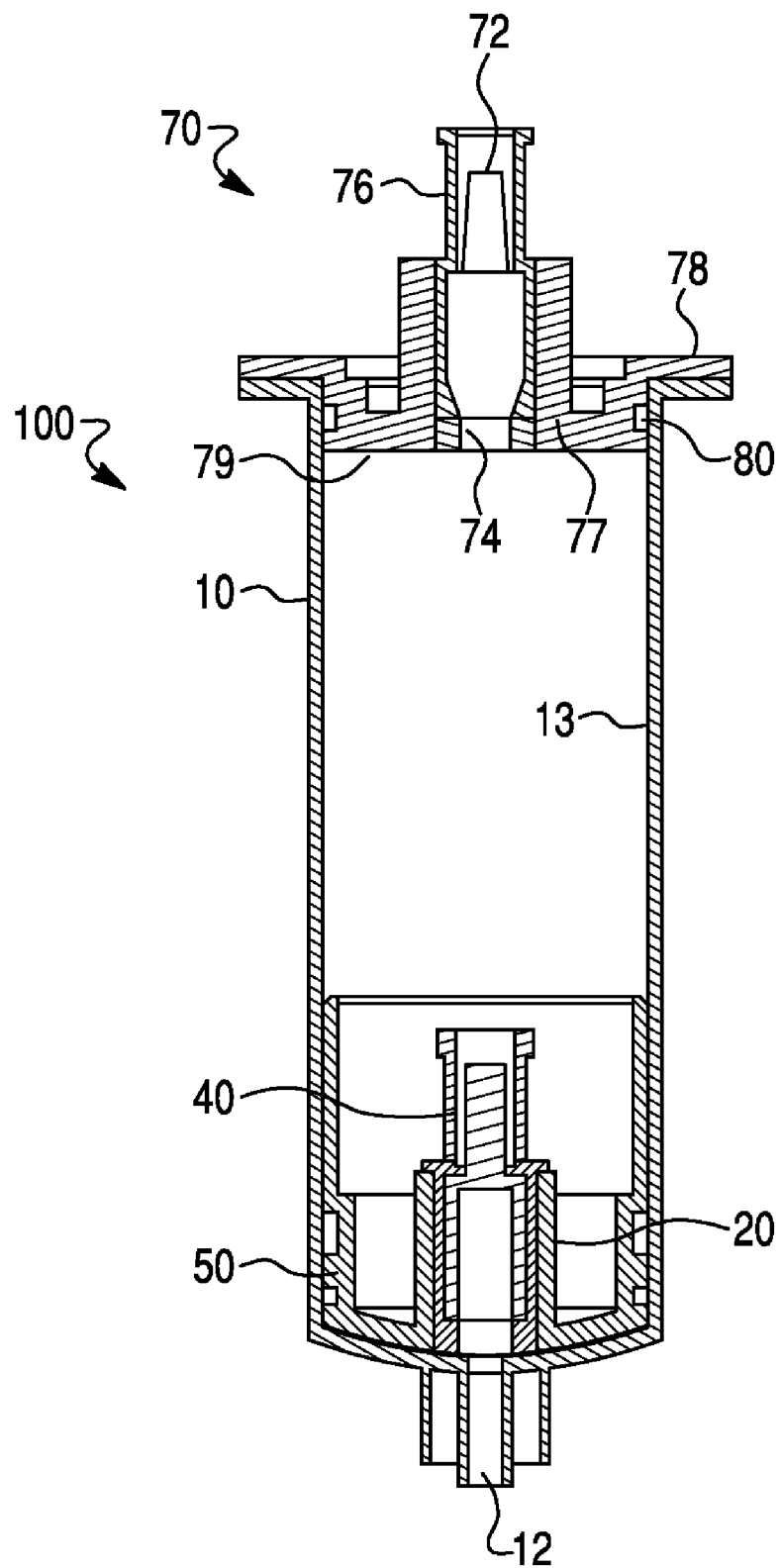
FIG. 5 is a cross-sectional view of the component of the kit of FIG. 1C before aspiration of the biological fluid.

FIGS. 3A-3B show the removable element 30 before and after the biological fluid 500 is aspirated into the barrel 10 through the first static opening 12, respectively. As shown in FIG. 3A, at least a portion of the removable element 30 fits within the barrel 10 and engages the piston assembly 20. Specifically, the snapping elements 32 or snaps 32 of the removable element 30 engage the piston assembly 20. The engagement of the snapping elements 32 to the piston assembly 20 allows a user to grip the finger flange 36 of the removable element 30 and pull the removable element 30 and the piston assembly 20 in the proximal direction. As the removable element 30 is pulled out of the barrel 10, biological fluid 500 enters the barrel through the first opening 12. The movement of the removable element 30 within the barrel 10 has no affect on the opening or closing of the shut-off valve 40 because the engagement of the snapping elements 32 to the piston assembly 20 does not affect the active element 42 of the shut-off valve 40. The biological fluid 500 may be any suitable fluid. For example, the biological fluid may be platelet-rich plasma.

As the removable element 30 is pulled out of the barrel 10, the release knobs 37 are moved toward a position where they will no longer be located within the barrel 10. When the release knobs 37 are outside of the barrel 10, a sufficient amount of the biological fluid 500 has entered the barrel 10 and the release knobs 37 may be pressed so that the snapping elements 32 can be disengaged from the piston assembly 20. Much as the engagement of the snapping elements 32 to the piston assembly 20 does not affect the active element 42 of the shut-off valve 40, the disengagement of the snapping elements 32 to the piston assembly 20 does not affect the active element 42.

After the biological fluid 500 has finished aspirating through the first static opening 12, a plug 15 or valve (not shown) is inserted into the first static opening 12 to prevent the biological fluid 500 from exiting the barrel 10. The plug 15 may be any suitable plug. For example, the plug 15 may be a luer plug.

The removable element 30 most conveniently aspirates biological fluid when the diameter of the barrel 10 is smaller and when the volume of biological fluid that can be aspirated into the barrel 10 is smaller. The greater the volume of biological fluid that can be aspirated in the barrel 10, the more cumbersome it gets for the operator of the kit 100 to manually aspirate the biological fluid into the barrel 10 using the removable element 30. For example, when about 50 ml of biological fluid can be aspirated into the barrel 10, it gets more cumbersome for the operator of the kit 100 to manually aspirate the biological fluid into the barrel 10 of the removable element 30. When the diameter of the barrel 10 is smaller, the rate at which the biological fluid aspirates into the barrel 10 is relatively fast because there is a smaller volume for which the piston assembly 20 must travel. As the diameter of the barrel 10 increases, however, the rate at which the biological fluid aspirates into the barrel 10 decreases. For instance, aspiration of larger doses of biological fluid, e.g., 20-30 ml, when the diameter of the barrel 10 increases, may take as long as 30 to 60 seconds. The longer time may inconvenience the person operating the kit 100 and may inhibit safety of using the kit 100.

Referring to FIGS. 5-7B, a removable element 70 is shown that comprises a static plug 70 and a static shut-off valve 72 or shut-off valve 72 or static plug valve 72. Unlike the removable element 30, the removable element 70 does not inconvenience the person operating the kit 100 or inhibit safety of using the kit 100 when the diameter of the barrel 10 is larger. The static plug 70 allows the person operating the kit 100 to generate a vacuum within the kit 100. The vacuum turns the kit 100 into an aspiration pump. After the kit 100 is connected to a biological fluid source, (e.g., an IV port, butterfly needle, etc.), the person operating the kit 100 takes a specific volume of air off the kit 100. Because the removable element 70 includes a shut-off valve 72, the removable element 70 is able to maintain the vacuum inside the barrel 10 and the piston assembly 20 is able to move in the proximal direction, thereby aspirating a desired amount of biological fluid into the barrel 10. The desired amount of biological fluid is accurately obtained in the barrel 10 because the removable element 70 includes a mechanical stop that stops the piston assembly 20 from moving in the proximal direction when aspiration of the biological fluid is completed.

The static plug 70 may include a base 77 and stopping elements 78. The base 77 is positioned within the barrel 10 of the kit 100. The base 77 is flush with the inner sides of the barrel 10 and the stopping elements 78 extend from the base 77 in an axial direction.

Additionally, the static plug 70 may include a seal 80, a valve housing 74, and a valve connector 76. The seal 80 enables the static plug 70 to seal a proximal end 79 of the bore 13 of the barrel 10. The seal 80 is similar to the seal 50 of the removable element 30. For example, the seal 8—may be an O-ring seal 80. The valve housing 74 houses the shut-off valve 72. The valve connector 76 may be similar in structure to the valve housing 44, active element 42, and luer connector 46. For example, the valve connector 76 opens the shut-off valve 72 when the valve connector 76 is engaged by a suitable external element (e.g., external syringe or vacuum pump).

The shut-off valve 72 is positioned within the static plug 70 and is configured to create a vacuum within the barrel 10. The shut-off valve 72 creates a vacuum within the barrel 10 when the valve connector 76 is engaged by the suitable external element.

The removable element 70 is configured to aspirate biological fluid through the first static opening 12 of the barrel 10. The removable element 70 is also configured to move the piston assembly 20 so that the first static opening 12 receives the biological fluid.

As shown in FIG. 6A, before the removable element 70 aspirates biological fluid through the first static opening 12 of the barrel 10, the static plug 70 is separated from the piston assembly 20 by an axial distance 90 or lengthwise distance 90. The distance 90 is set in accordance with the required amount of biological fluid that needs to be aspirated. To generate the required vacuum to allow aspiration of the biological fluid within the barrel 10 an air volume that is greater than a predetermined volume 92 or initial vacuumed compartment 92 must be taken out of the barrel 10.

When the valve connector 76 is engaged by the suitable external element, the piston assembly 20 travels the distance 90 and moves toward the proximal side of the barrel 10 (see FIGS. 6A-6B). As the piston assembly 20 moves toward the proximal side of the barrel 10, the biological fluid 500 enters the barrel 10. FIG. 6B shows the kit 100 after the piston assembly 20 has traveled the distance 90. The base 77 provides a mechanical stop for the piston assembly 20 to ensure that amount of biological fluid 500 aspirated does not exceed the required amount of biological fluid. Because the vacuum level decays as the piston assembly 20 moves travels the distance 90, the vacuum level within a volume 93 or concluded vacuum compartment 93 is significantly lower than the predetermined volume 92. A minimum vacuum, however, is still maintained to ensure completion of the aspiration and overcome friction. The minimum vacuum is known as the residual vacuum.

Figure 7A:
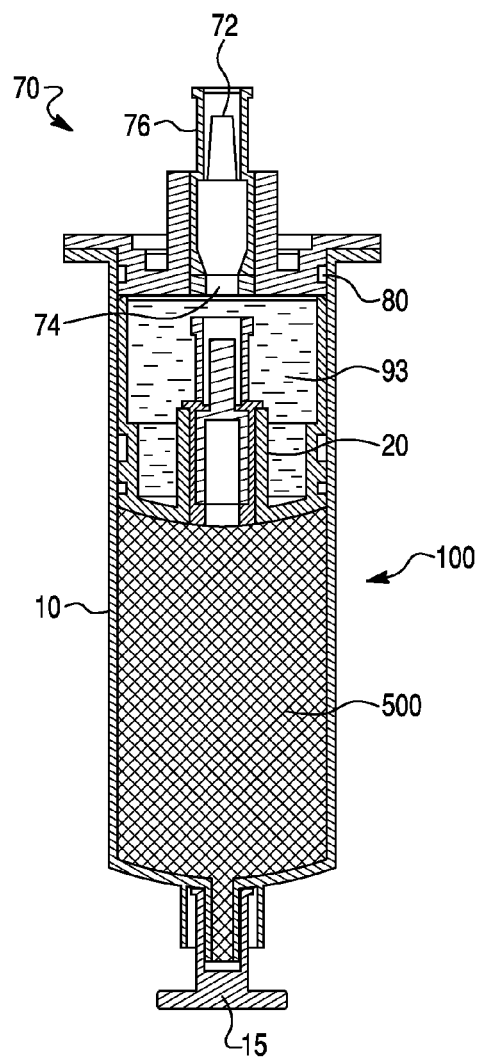
FIG. 7A is a cross-sectional view of the component of the kit of FIG. 1C after aspiration of the biological fluid and after a plug has been inserted into a first opening.
Figure 7B:
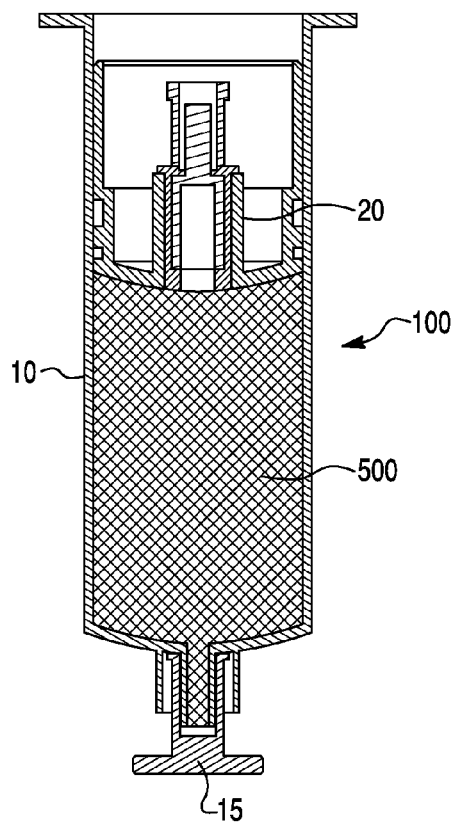
FIG. 7B is a cross-sectional view of the component of the kit of FIG. 1C after the removable element has been removed from the kit.

After the biological fluid 500 is aspirated into the barrel 10, a plug 15 or valve is inserted into the first static opening 12 (see FIG. 7A) and the removable element 70 is removed from the barrel 10 (see FIG. 7B). The plug 15 prevents the biological fluid 500 from exiting the barrel 10. The plug 15 may be any suitable plug. For example, the plug 15 may be a luer plug. The residual low level vacuum 93 does not prevent the ability to remove the static plug 70 from the barrel 10 or bring the kit 100 into a position where centrifugation may occur.

As shown in FIGS. 8A-8B, after the plug 15 or valve is inserted into the first static opening 12 and the removable element 30, 70 is removed from the barrel 10, centrifugation occurs. During centrifugation, the biological fluid is separated into components 502, 504. For example, if the biological fluid 500 is platelet-rich plasma, the first component 502 may include a residue or red blood cells and the second component 504 or constituent 504 may include plasma. Any suitable method of centrifugation may be used to separate the biological fluid into separate components.

After centrifugation, it should be appreciated that removal of the second component 504 is required, while the goal is to minimize the risk of contaminating or mixing the second component 504 with the first component 502 or residue.

Figure 9:
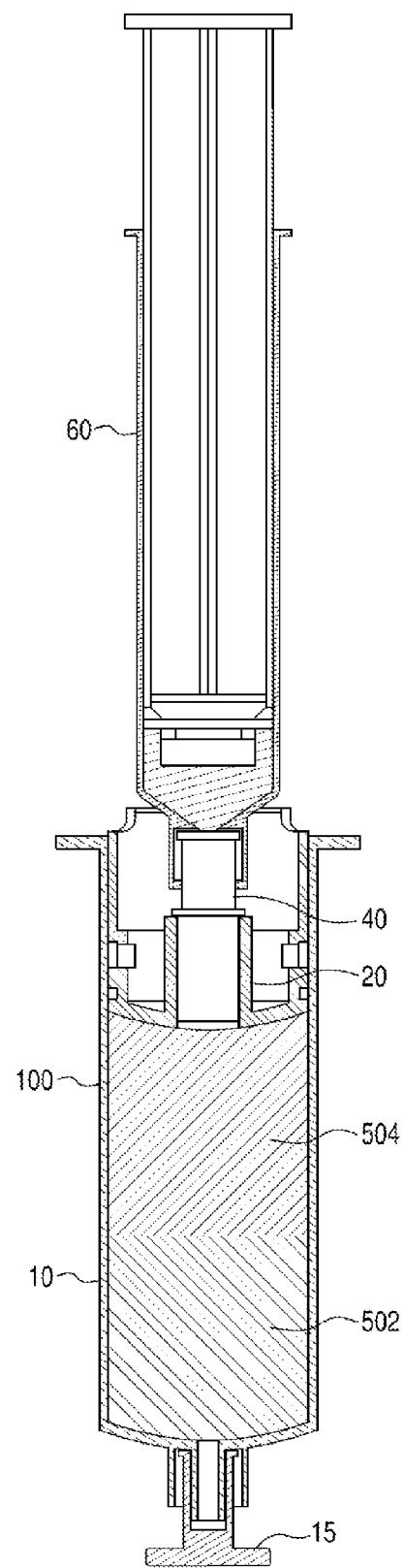
FIG. 9 is a cross section of the component of the kit of FIG. 1D before a constituent of the biological fluid is drained.
Figure 10A:
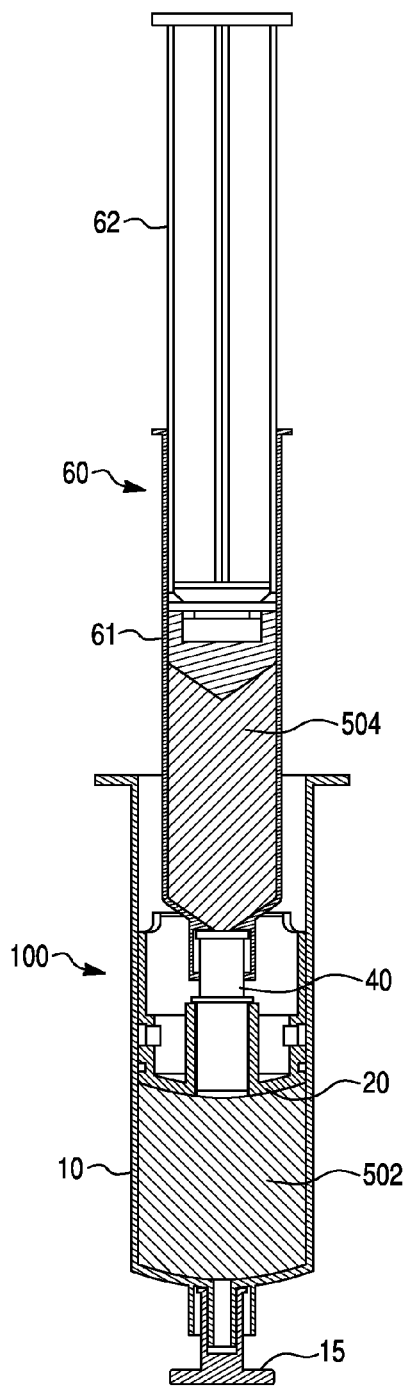
FIG. 10A is a cross section of the component of the kit of FIG. 1D while the constituent of the biological fluid is drained.
Figure 10B:
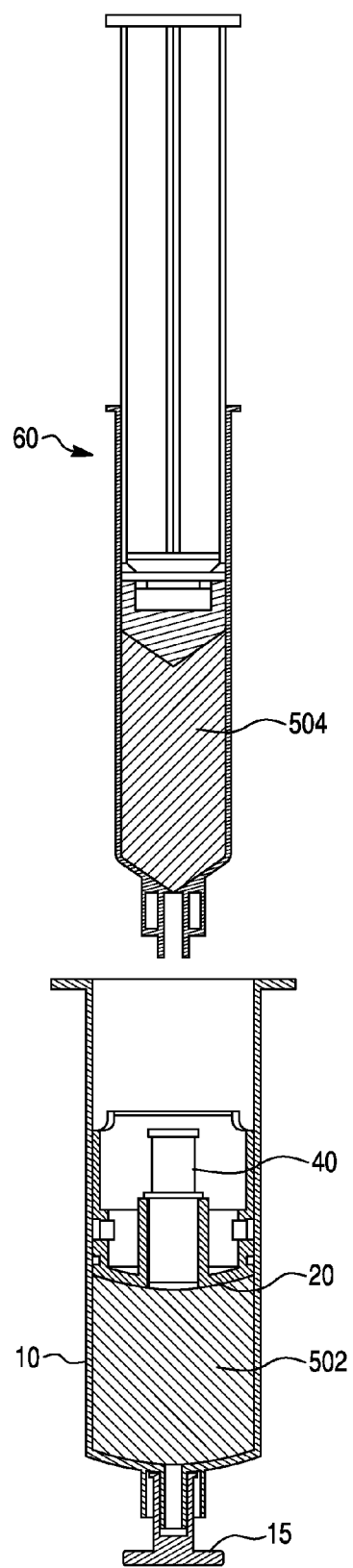
FIG. 10B is a cross section of the component of the kit of FIG. 1D after the constituent of the biological fluid is drained.

As shown in FIGS. 9-10B, a drainage element 60 may be used to remove the second component 504 from the barrel 10. The drainage element 60 is configured to engage the shut-off valve 20 of the piston assembly 40, such that the shut-off valve 20 opens and the second movable opening receives the constituent 504. Specifically, the drainage element 60 engages the active element 42 of the piston assembly 20. When the drainage element 60 connects to the luer connector 46 of the active element 42 (see FIG. 9), thereby engaging the active element 42, the shut-off valve 40 opens. When the shut-off valve 40 opens, a fluid path to the movable second opening opens. The drainage element 60 may be any suitable element that is configured to engage the shut-off valve 20 and drain the constituent 504. For example, the drainage element 60 may include a male luer (not shown) or a syringe 60.

If the drainage element 60 is a syringe 60, the drainage element may include a barrel 61 and a rod 62. The barrel 61 of the drainage element 60 receives the constituent 504 and the rod 62 moves in the proximal direction when the barrel 61 receives the constituent 504. Specifically, when the drainage element 60 is pushed in the distal direction, as shown in FIG. 10A, the constituent 504 is expelled toward the proximal direction into the barrel 61 of the drainage element 60. As the constituent 504 enters the barrel 61, the rod 62 moves in the proximal direction.

Once the constituent 504 is contained within the barrel 61 of the drainage element 60, the drainage element 60 is disengaged from the luer connector 46 of the active element 42 (FIG. 10B). Once the drainage element 60 is disengaged, the barrel 10 only contains the first component 502 and the fluid path to the movable second opening closes because the shut-off valve 40 closes. After the drainage element 60 is disengaged, the constituent 504 is ready for further processing. For example, the constituent 504 may be mixed with additional ingredients to create an autologous formula or the constituent 504 may again undergo centrifugation.

Figure 11:
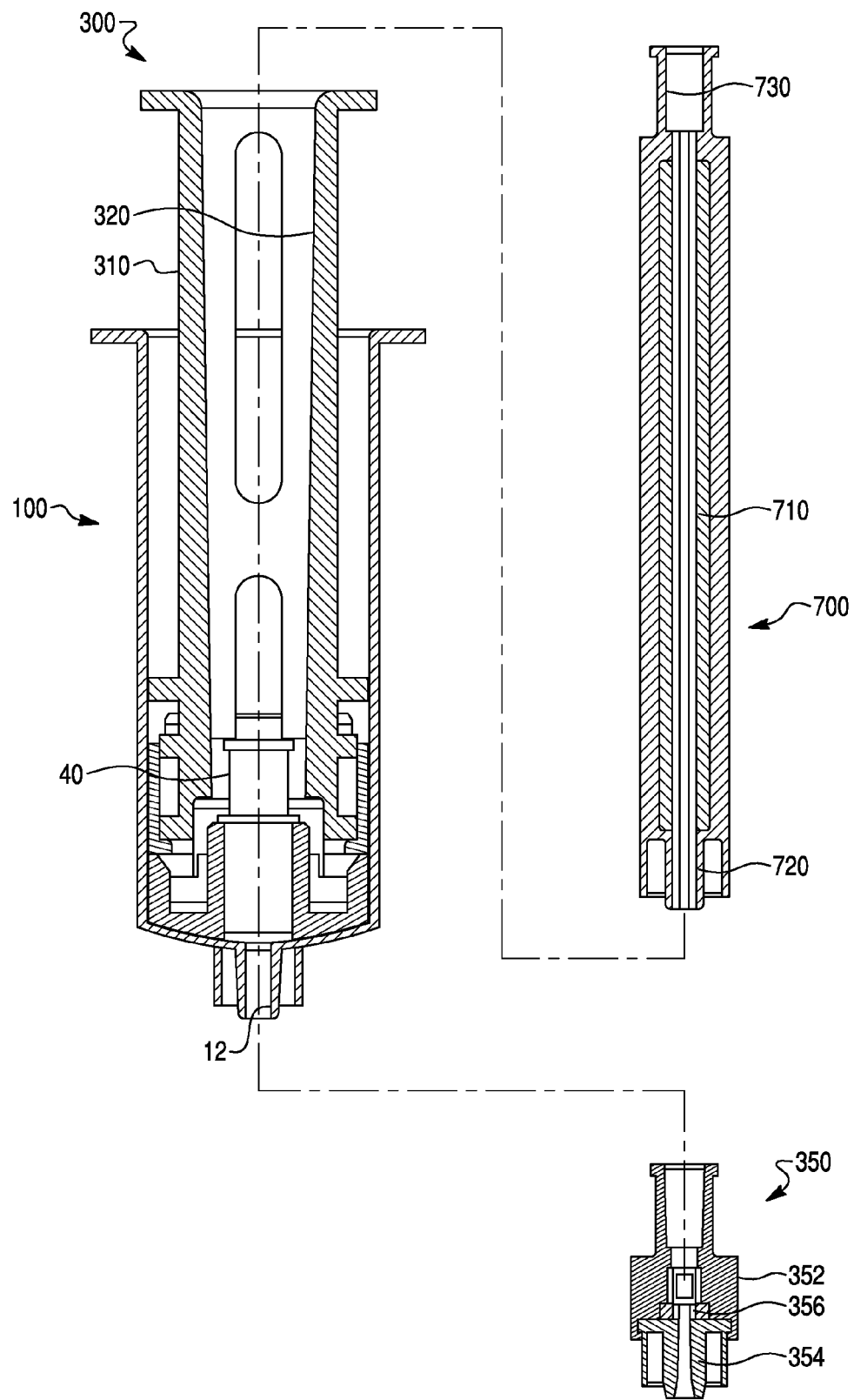
FIG. 11 is a cross section, partially exploded view of the component of the kit of FIG. 1E before a substance is added to the barrel.
Figure 12A:
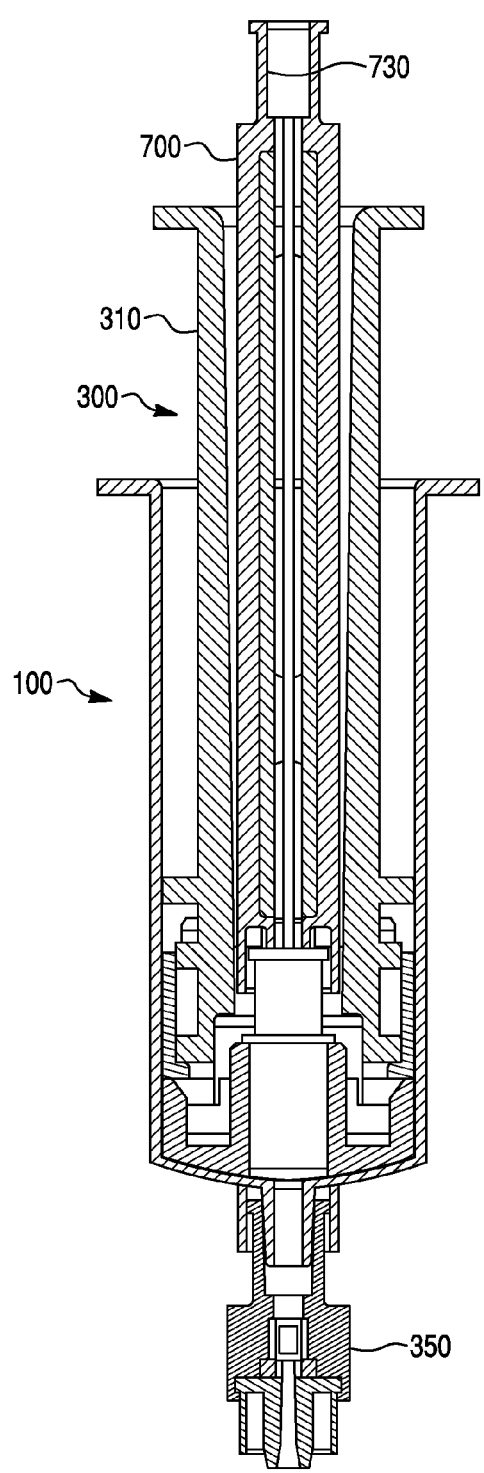
FIG. 12A is a cross section of the component of the kit of FIG. 1E before the substance is been added to the barrel.
Figure 12B:
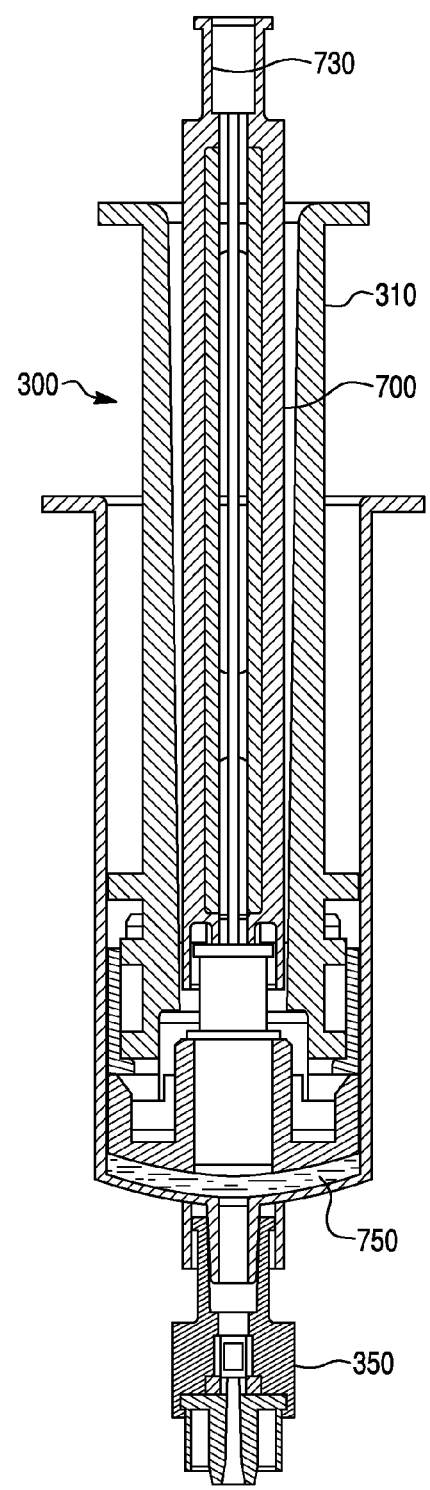
FIG. 12B is a cross-sectional view of the component of the kit of FIG. 1E after the substance is added to the barrel.
Figure 13:
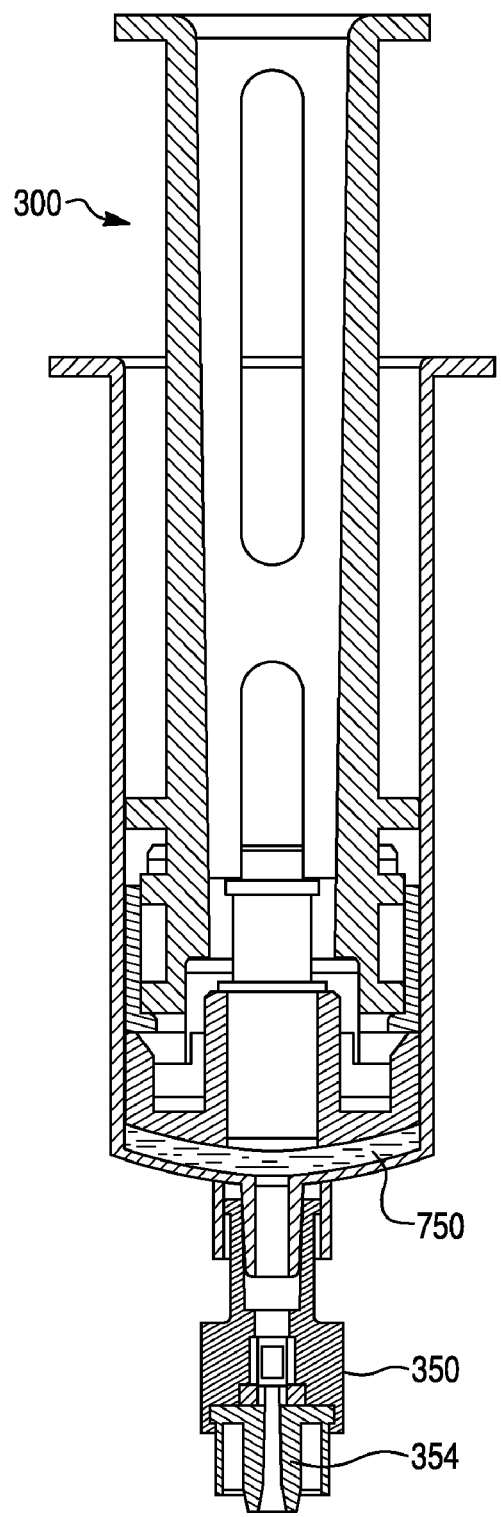
FIG. 13 is a cross-sectional view of the component of the kit of FIG. 1E after the substance is added to and the adapter element is removed from the barrel.

As shown in FIGS. 11-13, the kit 100 may also include the interacting element 300 and a sealing element 350. The interacting element 300 is configured to engage the shut-off valve 40, such that the shut-off valve 40 opens and the second movable opening receives a substance 750 before the biological fluid enters the barrel 10. When the interacting element 300 engages the shut-off valve 40, at least a portion of the interacting element 300 is positioned within the barrel 10. The interacting element 300 may engage the shut-off valve 40 before the biological fluid is aspirated into the barrel 10 using the removable element 30 or the removable element 70. The substance 750 may be any substance desired to mix with the biological fluid. For example the substance 750 may be an anti-coagulant.

The interacting element 300 comprises a rod 310 and an adapter element 700. The adapter element 700 is configured to transport the substance 750. A portion of the adapter element 700 is positioned in an inner diameter 320 of the rod 310. The adapter element 700 comprises a housing 710, an engagement element 720, and a proximal connector 730. The housing 710 is configured to create a fluid path for the substance 750 between the engagement element 720 and the proximal connector 730. The engagement element 720 forms a distal end of the housing 710 and is configured to engage with and open the shut-off valve 40. The engagement element 720 may be any suitable element. For example, the engagement element 720 may be a male luer connector. The proximal connector 730 is adjacent to a proximal end of the housing 710 and is configured to receive the substance 750 from a suitable element (not shown). The proximal connector 730 may be any suitable element that can house the substance 750. For example, the proximal connector 730 may be a female luer connector. The suitable element, from which the proximal connector 730 receives the substance 750 may be, for example, a syringe that includes a male luer connector able to connect to the proximal connector 730. When the proximal connector 730 is connected to the suitable element and when the engagement element 720 opens the shut-off valve 40, the fluid path in the housing 710 is open and the substance 750 may be transferred from the suitable element to the proximal connector 730, from the proximal connector 730 to the housing 710, through the housing 710 to the engagement element 720, and from the engagement element 710 to the inside of the syringe 300.

To prevent the substance 750 from leaking out of the barrel 10 through the first static opening 12, the first static opening 12 must be closed by the sealing element 350. The sealing element 350 is configured to seal the first static opening 12 when the shut-off valve opens 40 so that the substance 750 does not exit the barrel 10 through the first static opening 12. The sealing element 350 may be any suitable element. For example, the sealing element 350 may be a one-way check valve 350 (see FIGS. 11-13) or a plug (not shown). If the sealing element 350 is a one-way check valve, the sealing element 350 may include a first luer connector 352 or female luer connector 352 and a second luer connector 354 or male luer connector 354. The luer connectors 352, 354 are able to engage one another around an element 356 (e.g., a duck-bill type valve, an umbrella valve, a butterfly valve, etc). The luer connectors may be made of any suitable material, for example biocompatible plastic, and the element 356 may be made of any suitable material, for example, biocompatible rubber. The sealing element 350 helps prevent the operator of the kit 100 from injecting anti-coagulant into a patient's vein.

The kit 100 thus allows for drainage of all or part of the kit's 100 contents in a safe manner without the usage of sharp elements and with minimal exposure to additional biological fluids because the movable second opening allows draining of all or a part of the kit's contents through the proximal side of the kit 100 while the first static opening 12 is plugged. The contents, such as the constituent 504, are able to be drained into a clean, sterile drainage element or container 60, thereby preventing contamination by residues (e.g. RBC or red blood cells) that may be left in the barrel 10 of the kit 100. Specifically, the biological fluid 500 enters the kit 100 through the first static opening 12 and the constituent 504 exits through the movable second opening. The movable second opening is not used until the constituent 504 exits the barrel 10 of the kit 100. Accordingly, the constituent 504 is not contaminated by the biological fluid 500 because the constituent 504 exits the barrel 10 through a different opening from which the biological fluid 500 enters the barrel 10. The first component 502, which remains in the barrel 10 after the drainage element 60 drains the constituent 504 from the barrel 10, can be safely disposed of without requiring the first component 502 to be drained from the kit 100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the kit for containing biological fluid and draining a constituent of the biological fluid as shown in the various exemplary embodiments is illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present embodiments.

What is claimed is:

1. A kit for containing biological fluid and draining a constituent of the biological fluid, the kit comprising:
   (A) a barrel, which has a first static opening for receiving the biological fluid;
   (B) a piston assembly, disposed within the barrel, that comprises a shut-off valve, wherein the shut-off valve is configured to form a second movable opening for receiving or draining the constituent when the shut-off valve is engaged to be open;
   (C) a removable element that is configured to aspirate the biological fluid through the first static opening, wherein the removable element is configured to move the piston assembly, without engaging the shut-off valve, so that the first static opening receives the biological fluid;
   (D) a drainage element configured to engage the shut-off valve, such that the shut-off valve opens and the second movable opening receives the constituent; and
   (E) an interacting element, at least a portion of which is positioned in the barrel and which is configured to engage the shut-off valve, such that the shut-off valve opens and the second moveable opening receives a substance, and a sealing element that is configured to seal the first static opening when the shut-off valve opens, wherein the interacting element comprises (a) a rod and (b) an adapter element, a portion of which is positioned in the rod, that is configured to transport the substance.

2. The kit of claim 1, wherein the biological fluid comprises platelet-rich plasma.

3. The kit of claim 1, wherein the constituent comprises plasma.

4. The kit of claim 1, wherein the removable element comprises:
(a) a shaft,
(b) snapping elements, coupled to the shaft that are configured to engage the piston assembly, and
(c) a stabilizing element, coupled to the shaft and adjacent to the snapping elements, that is configured to restrict radial movement of the shaft when the snapping elements engage the piston assembly, and
(d) release knobs configured to disengage the snapping elements only when the barrel contains a sufficient amount of the biological fluid.

5. The kit of claim 1, wherein the removable element comprises:
(a) a static plug that comprises (i) a base, within the barrel, and (ii) stopping elements, extending from the base in an axial direction, and
(b) a static shut-off valve, positioned within the static plug, that is configured to create a vacuum within the barrel.

6. The kit of claim 1, wherein the drainage element comprises a male luer or a syringe that is configured to engage the shut-off valve and drain the constituent.

7. The kit of claim 1, wherein the adapter element comprises:
(a) a housing,
(b) an engagement element, forming a distal end of the housing, that is configured to engage with and open the shut-off valve, and
(c) a proximal connector, adjacent to a proximal end of the housing, that is configured to receive the substance.

8. The kit of claim 7, wherein the housing is configured to create a fluid path between the engagement element and the proximal connector.

9. The kit of claim 1, wherein the sealing element is a check valve, enabling flow only into the barrel, or a plug.

10. The kit of claim 1, wherein the substance is anti-coagulant.

* * * * *